(12) United States Patent
Kurahashi et al.

(10) Patent No.: US 8,476,198 B2
(45) Date of Patent: Jul. 2, 2013

(54) FUNGICIDAL COMPOSITION

(75) Inventors: Makoto Kurahashi, Hyogo (JP); Franklin Paul Silverman, Highland Park, IL (US); Jennifer C. Kochan, Palatine, IL (US); Nicole Higgs, Racine, WI (US); Dale O. Wilson, Jr., Round Lake Beach, IL (US); Peter D. Petracek, Grayslake, IL (US); Gregory D. Venburg, Deerfield, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 315 days.

(21) Appl. No.: 12/763,621

(22) Filed: Apr. 20, 2010

(65) Prior Publication Data

US 2010/0267565 A1    Oct. 21, 2010

Related U.S. Application Data

(60) Provisional application No. 61/170,745, filed on Apr. 20, 2009.

(51) Int. Cl.
*A01N 37/10*   (2006.01)
*A01N 25/32*   (2006.01)
*A01N 43/26*   (2006.01)

(52) U.S. Cl.
USPC ............... 504/322; 504/103; 514/383

(58) Field of Classification Search
USPC .................. 504/322, 103; 514/383
See application file for complete search history.

(56) References Cited

U.S. PATENT DOCUMENTS

| 4,528,020 | A  | * | 7/1985 | Kolc et al. ............... 71/28 |
| 5,714,507 | A  |   | 2/1998 | Valcke et al. |
| 6,740,671 | B2 | * | 5/2004 | Kang et al. .............. 514/370 |
| 2003/0050194 | A1 | * | 3/2003 | Hopkinson et al. ........ 504/363 |
| 2007/0213225 | A1 |   | 9/2007 | Hofer et al. |

FOREIGN PATENT DOCUMENTS

| JP | 11255607 A | * | 9/1999 |
| WO | WO 99/45774 |   | 9/1999 |

OTHER PUBLICATIONS

Itagaki et al., "Biological activities and structure-activity relationship of substitutation compounds of N-[2-(3-indolyl)ethyl]succinamic acid anf N-[2-(1-naphthy)ethyl]succinamic acid, derived from a new category of root-promoting substances, N-(phenethyl)succinamic acid analogs", Plant and Soil 2003, 255: pp. 67-75.

* cited by examiner

*Primary Examiner* — Fereydoun G Sajjadi
*Assistant Examiner* — Courtney Brown
(74) *Attorney, Agent, or Firm* — Wood, Philips, Katz, Clark & Mortimer

(57) ABSTRACT

A treatment of N-(phenylethyl)succinamic acid or its salts provides enhancement of fungicide activity of a fungicide azole compound, and thus, a fungicidal composition comprising a fungicide azole compound and N-(phenylethyl)succinamic acid or its salts is effective for controlling plant diseases and may also enhance plant growth.

15 Claims, No Drawings

FUNGICIDAL COMPOSITION

FIELD OF THE INVENTION

The present invention is directed to a fungicidal composition.

BACKGROUND OF THE INVENTION

Many fungicidal azole compounds are known and have been developed.

N-(2-phenylethyl)succinamic acid (PESA) is known as an active ingredient of a plant growth regulator according to WO 99/45774, which describes amido acids, including PESA, that can be used with a fungicidal compound having root-enhancing activity (e.g., hydroxyisoxazole, metasulfocarb, metalaxyl). However, it does not mention enhancement by PESA of fungicidal activity of a fungicidal compound. Moreover, it also does not teach that the combination of PESA or a PESA salt with an azole fungicide can improve plant growth.

SUMMARY OF THE INVENTION

The present invention provides a fungicidal composition comprising a fungicidal azole compound and at least one selected from the group consisting of N-(2-phenylethyl)succinamic acid (PESA) and its salts.

The present invention also provides for the use of PESA or its salts to enhance fungicidal activity of a fungicidal azole compound.

DETAILED DESCRIPTION OF THE INVENTION

In the present invention, the phrase "a fungicidal azole compound" means a fungicidal compound having a triazole or imidazole structure. It generally has sterol biosynthetic inhibiting activity. Examples of fungicidal azole compounds include azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, penconazole, pefurazoate, prochloraz, propiconazole, prothioconazole, simeconazole, tebuconazole, tetraconazole, triadimefon, triadimenol, triticonazole, and triflumizole.

Presently preferred fungicidal azole compounds include metconazole and triadimenol.

PESA is N-(2-phenylethyl)succinamic acid of the formula:

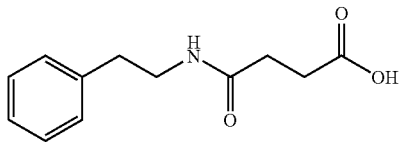 [SMILES: O=C(O)CCC(=O)NCCc1ccccc1]

which can be prepared by the method described in WO 99/45774.

In the present invention, any pesticidally acceptable salt of PESA can also be used as well as PESA. Namely, PESA or a mixture of two or more selected from the group consisting of PESA and its salts can be used. Examples of such salts include calcium, magnesium, potassium, sodium, ammonium and organic ammonium salts. The organic ammonium salts include the salts formed by neutralization of PESA by an amine bearing one, two or three groups selected from the group consisting of C1-C4 alkyl groups and C1-C4 hydroxyalkyl groups. Typical examples of organic ammonium salts include trimethylammonium salt, isopropylammonium salt, 2-hydroxyethylammonium salt (ethanolamine salt), 2-hydroxyethyldimethylammonium salt (dimethylethanolamine salt), bis(2-hydroxyethyl)ammonium salt (diethanolamine salt) and tris(2-hydroxyethyl)ammonium salt (triethanolamine salt). The presently preferred salt is the sodium salt.

The salts of PESA are produced, for example, by dissolving the free acid (PESA) in water and adding an equimolar amount of a base to the solution. In the case of the sodium salt, sodium hydroxide is preferably used as the base and this method allows for the production of a sodium salt solution ranging in concentration from 0.1 to 40% by weight.

The fungicidal composition comprises a fungicidal azole compound and PESA or its salts. The amount of PESA or its salts in the composition is an amount sufficient for enhancing fungicidal activity of the fungicidal azole compound, and is usually between 0.5 to 99 times by weight of the amount of the fungicidal azole compound. The amount of the fungicidal azole compound is usually 0.3 to 30% by weight, and the amount of PESA or its salts is usually 0.02 to 20% by weight of the fungicidal composition.

In another embodiment, the present invention provides a composition and method that further comprises utilizing clothianidin and metalaxyl with PESA and the fungicidal azole compound.

The fungicidal composition further comprises a carrier, and optionally auxiliaries for formulation. Examples of suitable auxiliaries include surfactants, dispersing agents, thickeners, stabilizing agents, antifreezing agents and colorants. The amount of the carrier is usually 10 to 99.5% by weight, preferably 50 to 99.5% by weight of the fungicidal composition, and the amount of the auxiliaries is usually 0 to 90% by weight, preferably 0.25 to 25% by weight.

Examples of solid carriers include powders and granules of clays such as kaoline clay, diatomaceous earth, bentonite, fubasami clay and terra alba; synthetic hydrated silica; talc; ceramic; other inorganic minerals such as sericite, quartz, sulfur, activated carbon, calcium carbonate and hydrated silica; and chemical fertilizers such as ammonium sulfate, ammonium phosphate, ammonium nitrate, ammonium chloride and urea. Examples of liquid carriers include aromatic and aliphatic hydrocarbons such as xylene, toluene, alkylnaphthalene, phenylxylylethane, kerosene, gas oil, hexane and cyclohexane; halogenated hydrocarbons such as chlorobenzene, dichloromethane, dichloroethane and trichloroethane; alcohols such as methanol, ethanol, isopropyl alcohol, butanol, hexanol, benzyl alcohol and ethylene glycol; ethers such as diethyl ether, ethylene glycol dimethyl ether, diethylene glycol monomethyl ether, diethylene glycol monoethyl ether, propylene glycol monomethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrlile and isobutyronitrile; sulfoxides such as dimethyl sulfoxide (DMSO); amides such as N,N-dimethylformamide, N,N-dimethylacetamide and N-methylpyrollidone; alkylydene carbonates such as propylene carbonate; vegetable oils such as soybean oil and cotton seed oil; plant essential oils such as orange oil, hyssop oil and lemon oil; and water. Examples of gasous carriers include butane gas, flon gas, liquefied petroleum gas (LPG), dimethyl ether and carbon dioxide. When the fungicidal composition contains a carrier, the amount of the carrier is usually 1 to 99% by weight of the fungicidal composition.

Examples of surfactants include alkylsulfate salts, alkylsulfonate salts, alkylarylsulfonate salts such as alkylbenzenesulfonate salts and alkylnaphthalenesulfonate salts, polyoxyethylene alkyl ether phosphate salts, alkylaryl ethers, polyoxyethylene alkylaryl ethers, polyethylene glycol ethers, polyvalent alcohol esters and sugar alcohols. When the fungicidal composition contains a surfactant, the amount of the surfactant is usually 0.5 to 20% by weight of the fungicidal composition.

Examples of dispersing agents include calcium ligninsulfonate, methylcellulose and hydroxymethylcellulose. When the fungicidal composition contains a dispersing agent, the amount of the dispersing agent is usually 0.25 to 25% by weight of the fungicidal composition.

Examples of thickeners include aluminum magnesium silicate, gum arabic, polyvinyl alcohol and polyvinylpyrrolidone. When the fungicidal composition contains a thickener, the amount of the thickener is usually 0.1 to 10% by weight of the fungicidal composition.

Examples of stabilizing agents include BHT (2,6-di-tert-butyl-4-methylphenol) and BHA (mixture of 2-tert-butyl-4-methoxyphenol and 3-tert-butyl-4-methoxyphenol). When the fungicidal composition contains a stabilizing agent, the amount of the stabilizing agent is usually 0.01 to 10% by weight of the fungicidal composition.

Examples of antifreezing agents include ethylene glycol, propylene glycol, trimethylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like, diethylene glycol, triethylene glycol, tetraethylene glycol, polyoxyethylene or polyoxypropylene glycols of molecular weight up to about 4000, diethylene glycol monomethyl ether, diethylene glycol monoethyl ether, triethylene glycol monomethyl ether, butoxyethanol, butylene glycol monobutyl ether, dipentaerythritol, tripentaerythritol, tetrapentaerythritol, diglycerol, triglycerol, tetraglycerol, pentaglycerol, hexaglycerol, heptaglycerol and octaglycerol. When the fungicidal composition contains an antifreezing agent, the amount of the antifreezing agent is usually 0.1 to 10% by weight of the fungicidal composition.

Examples of colorants include azo dyestuffs and anthraquinone dyestuffs. When the fungicidal composition contains a colorant, the amount of the colorant is usually 0.01 to 1.0% by weight in the fungicidal composition.

The fungicidal composition of the present invention is prepared by conventional methods, for example, by mixing a fungicidal azole compound, PESA or its salts, a carrier and optionally auxiliaries, and further pulverization, granulation and so on. The fungicidal composition of the present invention can be a variety of formulations: dry flowables (DF), liquid flowables (LF), true liquids (TL), emulsifiable concentrates (EC), dusts (D), wettable powders (WP), suspoemulsions (SE), water-dispersible granules (WG) and others. Some are registered for use only by commercial applicators using closed application systems, others are readily available for on-farm use as dusts, slurries, water soluble bags, or liquid ready-to-apply formulations.

The application dosage of the fungicidal composition of the present invention is usually 0.01 to 10.0 kg/km$^2$, preferably 0.05 to 5 kg/kin$^2$ of the amount of the fungicidal azole compound.

The method of the present invention is a new use of PESA or its salts for enhancing fungicidal activity of a fungicidal azole compound by treatment with PESA or its salts. It is performed by applying PESA or its salts in combination with a fungicidal azole compound to plants. The plant can be any part and in any stage, for example, seed, tuber, bulb, root, leaf, stem and sprout. PESA or its salts may also be applied to surroundings of the plant, for example, soil. The soil treatment can be performed by application on the soil surface, application by mixing with soil, or the like. PESA or its salts are used in an effective amount for enhancing fungicidal activity of a fungicidal compound. The amount of PESA or its salts used in the invention depends on the fungicidal azole compound, and is generally 0.25 to 10 times by weight of the amount of the fungicidal azole compound. The method can be performed by applying the fungicidal composition of the present invention to plants or surroundings of the plants, or it can be performed by application of a dilution comprising PESA or its salts. The dilution usually contains PESA or its salts in 0.1 to 10% by weight and is applied to plants or surroundings of the plants, wherein an effective amount of the fungicidal azole compound is applied in advance or after the application of PESA or its salts. The method also can be performed by using the fungicidal composition of the present invention, namely, by the application of the fungicidal composition.

The fungicidal composition of the present invention is used for controlling plant diseases as well as protecting cultivated plants. Examples of the plant diseases include plant diseases caused by *Pythium, Tilletia, Gerlachia, Septoria, Ustilago, Fusarium, Rhizoctonia, Phytophthora, Plasmopara, Pseudoperonospora, Bremia, Botrytis, Pyrenophora, Monilinia, Magnaporthe, Cochliobolus, Gibberella, Blumeria, Erysiphe, Puccinia, Micronectriella, Typhula, Pseudocercosporella, Mycosphaerella, Stagonospora, Microdochium, Rhynchosporium, Gloeocercospora, Cercospora, Diaporthe, Elsinoe, Penicillium, Valsa, Podosphaera, Alternaria, Venturia, Colletotrichum, Diplocarpon, Botryosphaeria, Helicobasidium, Gymnosporangium, Cladosporium, Phomopsis, Glomerella, Uncinula, Phakopsora, Guignardia, Gloeosporium, Sphaerotheca, Cercosporella, Plasmodiophora, Peronospora Spongospora, Exobasidium, Pestalotiopsis, Sclerotinia, Aphanomyces, Bremia, Aspergillus, Tricoderma, Thielaviopsis, Phizopus, Mucor, Corticium,* and *Diplodia.*

Especially suitable target plants are potato, cereals (wheat, barley, rye, oats, rice), maize (corn), sugar beet, cotton, millet varieties such as sorghum, sunflower, bean, peas, oil plants (such as canola, rape and soybean), cabbage, tomato, eggplant, pepper, and other vegetables and spices, as well as woody perennials, ornamental shrubs, turfgrass, and flowers.

The fungicidal composition of the present invention is especially suitable for controlling disease of wheat caused by *Erysiphe graminis., Puccinia* spp., *Fusarium* spp., *Microdochium nivale, Ustilago tritici, Tilletia caries,* or *Mycosphaerella graminicola,* disease of barley caused by *Erysiphe graminis, Puccinia* spp., *Fusarium* spp., *Microdochium nivale, Ustilago nuda, Rhynchosporium secalis,* or *Pyrenophora teres,* disease of maize (corn) caused by *Fusarium* spp., *Puccinia polysora., Ustilago maydis,* or *Cercospola zeae-maydis,* disease of rape caused by *Screlotinia sclerotiorum,* disease of cotton caused by *Fusarium* spp., disease of soybeans caused by *Fusarium* spp. or *Phakopsora pachyrhizi,* disease of turfgrass caused by *Screlotinoa homoeocarpa* or *Rhizoctonia solani,* disease of rice caused by *Rhizoctonia solani,* disease of wheat caused by *Fusarium* spp., and disease of peas caused by *Fusarium solani.*

Suitable target plants also include transgenic crop plants of the foregoing varieties. The transgenic crop plants treated according to the invention are plants including propagation material thereof, which are transformed by recombinant DNA technology so that they are capable of synthesizing selectively acting toxins, such as, for example, from toxin-producing invertebrates, especially of the phylum Arthropoda; from *Bacillus thuringiensis* strains; from plants, such as lectins; or in the alternative, capable of expressing a herbicidal or fungicidal resistance.

A presently preferred application method of the fungicidal composition of the present invention is seed treatment. Further, a presently preferred application method of PESA or its salts in the method of the present invention is also seed treatment. In seed treatment, the application amount of the fungicidal composition of the present invention is usually 1 to 200 g, preferably 5 to 100 g per 100 kg of seeds in the amount of the fungicidal azole compound. The seed treatment can be performed by conventional methods, namely spraying liquid to seeds, coating seeds by powder, soaking seeds in liquid and so on.

EXAMPLES

The present invention will be explained in detail by the following representative examples. In the examples, part/parts mean part/parts by weight.

Formulation Example 1

One and a quarter parts of PESA, 2.5 parts of metconazole, 14 parts of polyoxyethylene styrylphenyl ether, 6 parts of calcium dodecylbenzenesulfonate and 76.25 parts of xylene are mixed well to give an emulsifiable concentrate.

Formulation Example 2

Five parts of PESA, 5 parts of metconazole, 35 parts of a mixture of precipitated silica and polyoxyethylene alkyl ether sulfate ammonium (1:1 by weight) and 55 parts of water are mixed and finely wet-pulverized to give a flowable formulation.

Formulation Example 3

Ten parts of PESA, 5 parts of metconazole, 1.5 parts of sorbitan trioleate and 28.5 parts of an aqueous solution containing 2 parts of polyvinyl alcohol, and 45 parts of an aqueous solution containing 0.05 part of xanthan gum and 0.1 part of aluminum magnesium silicate are added thereto, and then, 10 parts of propylene glycol are added thereto and mixed under stirring to give a flowable formulation.

Formulation Example 4

Five parts of PESA, 40 parts of metconazole, 5 parts of Soprophor FLK (Rhodia), 0.2 parts of ANTIFOAM C EMULSION (Dow Corning), 0.3 part of Proxel GXL (Arch Chemicals), and 49.5 parts of water are mixed and pulverized with glassbeads (f=1 mm), and finally the glassbeads are removed to give a flowable formulation.

Formulation Example 5

Fifty parts of PESA, 0.5 part of metconazole, 38.5 parts of NN kaolin clay (TAKEHARA KAGAKU KOGYO), 10 parts of Morwet D425 and 1.5 parts of Morwet EFW (AczoNobel) are mixed and pulverized by a jet mill to give a dust formulation.

Formulation Example 6

Four parts of PESA, one part of metconazole, one part of synthetic hydrated silica, 2 parts of calcium ligninsulfonate, 30 parts of bentonite and 62 parts of kaolin clay are mixed and pulverized well, kneaded with water, granulated and dried to give a granular formulation.

Formulation Example 7

Two parts of PESA, one part of metconazole, 87 parts of kaolin clay and 10 parts of talc are mixed and pulverized well to give a dust formulation.

Formulation Example 8

Forty parts of PESA, one part of metconazole, 3 parts of calcium ligninsulfonate, 2 parts of sodium lauryl sulfate and 54 parts of synthetic hydrated silica are mixed and pulverized well to give a wettable powder formulation.

Application Example 1

Five hundred milliliters of the emulsifiable concentrate of Fomulation example 1 is applied to 100 kg of sorgum seeds by a Seed dresser (Hans-Ulrich Hege GmbH) to give treated seeds.

Application Example 2

Fifty milliliters of the flowable formulation of Fomulation example 2 is applied to 10 kg of oilseed rape seeds by a Seed dresser (Hans-Ulrich Hege GmbH) to give treated seeds.

Application Example 3

Forty milliliters of the flowable formulation of Formulation example 3 is applied to 10 kg of rice seeds by a Seed dresser (Hans-Ulrich Hege GmbH) to give treated seeds.

Application Example 4

Ten parts of the flowable formulation of Formulation example 4, 10 parts of Pigment BPD6135 (SunChemical), and 80 parts of water are mixed, and 60 ml of the mixture is applied to 10 kg of corn seeds by a Seed dresser (Hans-Ulrich Hege GmbH) to give treated seeds.

Application Example 5

Fifty grams of the dust formulation of Formulation example 5 is applied to 10 kg of corn seeds to give treated seeds.

Application Example 6

Five hundred milliliters of the emulsifiable concentrate of Formulation example 1 is applied to 100 kg of sugarcane seeds by a Seed dresser (Hans-Ulrich Hege GmbH) to give treated seeds.

Application Example 7

Fifty milliliters of the flowable formulation of Formulation example 2 is applied to 10 kg of soybean seeds by a Seed dresser (Hans-Ulrich Hege GmbH) to give treated seeds.

Application Example 8

Fifty milliliters of the flowable formulation of Formulation example 3 is applied to 10 kg of wheat seeds by a Seed dresser (Hans-Ulrich Hege GmbH) to give treated seeds.

Application Example 9

Ten parts of the flowable formulation of Formulation example 4, 10 parts of Pigment BPD6135 (SunChemical), and 80 parts of water is mixed, and 70 ml of this mixture is applied to 10 kg of potato seed pieces by a Seed dresser (Hans-Ulrich Hege GmbH) to give treated seed pieces.

Application Example 10

Forty grams of the dust formulation of Formulation example 5 is applied to 10 kg of cotton seeds to give treated seeds.

Biological Example 1

Seed treatment effect against *Fusarium solani* f. sp. *pisi* (*Fusarium* root rot of pea)

PESA and metconazole were diluted with DMSO respectively and mixed with each other to obtain the desired material mixture. Then, this suspension was applied to pea seeds. The PESA solution and the metconazole solution were applied to seeds respectively for control, and DMSO for untreated control. The seeds were dried and planted in soil that was inoculated with *Fusarium solani* f. sp. *pisi*. After growing at 20-24° C. in a greenhouse, for 16 days, symptoms were investigated and the frequency of disease and % control were calculated. The fungicide interactions in the combinations are calculated according to Limpet's formula:

$E = X + Y - (X*Y)/100$

X=% action by active ingredient A using P ppm of active ingredient
Y=% action by active ingredient B using Q ppm of active ingredient
E=expected % action by active ingredients A and B using P and Q ppm of active ingredients If the action actually observed (O) is greater than the expected action (E), than the action of the combination is super-additive, i.e. there is a synergistic effect. In mathematical terms, synergism corresponds to a value of more than 100 for the ratio of O/E, said ratio O/E of less than 100 signals a loss of activity compared to the expected activity.

Synergy Effect=(Observed/Expected)*100

TABLE 1

Effect of metconazole and PESA on fungal control of *Fusarium solani* on pea.

| Ingredients | Appl. amount (gai/100 kg seed) | Observed action (% control) | Expected action (% control) | Synergy effect (%) |
|---|---|---|---|---|
| PESA | 10 | 9 | — | — |
| PESA | 2 | 0 | — | — |
| PESA + metconazole | 10 + 0.2 | 73 | 59 | 124 |
| PESA + metconazole | 2 + 1 | 91 | 73 | 125 |
| Metconazole | 1 | 73 | — | — |
| Metconazole | 0.2 | 55 | — | — |

This data shows that the combination of PESA and metconazole provides more effective disease control than metconazole alone.

Biological Example 2

Seeds of cotton were treated with PESA salt and/or triadimenol (BAYTAN® 30 Flowable Fungicide, Bayer Crop Science, RTP, NC USA). These were assayed in the pouch assay as described above. The addition of PESA salt protects or safens cotton from the negative effects of the fungicide on root growth.

TABLE 2

Effect of PESA salt and triadimenol on main root length (cm) of 6 day-old cotton seedlings.

| | Root Length (cm) | | | |
|---|---|---|---|---|
| Triadimenol g ai/100 lbs. of seed | 0 g ai of PESA salt/100 lbs. of seed | 25 g ai of PESA salt/100 lbs. of seed | 50 g ai of PESA salt/100 lbs. of seed | |
| 0 | 13.2 | 14.8 | 14.3 | |
| 28.2 | 12.8 | 13.9 | 15.1 | |
| 56.4 | 12.3 | 15.1 | 15.5 | | n = 8 pouches with three seedlings per pouch.

This data shows that the addition of PESA salt to triadimenol overcomes the negative effect of triadimenol on cotton root growth.

Biological Example 3

Seeds of spring wheat (*Triticum* spp.) were treated with a seed treatment containing metconazole (1.25 g/100 kg seed), metalaxyl (2.0 g/100 kg seed) and clothianaidin (10.0 g/100 kg seed). In one seed treatment batch, PESA salt (25 g/100 kg seed) was added. The seed was planted and grown in the Palouse area of Washington State, USA. After planting, the plots were assessed for plants/plot, white heads due to *Fusarium* root rot, and yield. The results of the study are shown in Table 3.

TABLE 3

Effect of PESA salt in spring wheat seed treatment on plants/plot, frequency of fusarium infection, and yield

| Treatment | Plants/plot | Number of plants with white heads (*Fusarium*) | Yield (grams wheat grains/square meter) |
|---|---|---|---|
| Untreated | 21 | 13.0 | 365.3 |
| Metconazole, Metalaxyl and Clothianidin | 28 | 10.8 | 545.8 |
| PESA salt, Metconazole, Metalaxyl and Clothianidin | 31 | 5.3 | 614.3 |

In this example, the combination of PESA with metconazole, metalaxyl and clothianidin promoted increased stand. Moreover, the presence of PESA in the seed treatment resulted in decreased *Fusarium* white head counts and increased final yield. Therefore, the addition of PESA to the seed treatment increased both fungicidal activity and yield.

The fungicidal composition of the present invention has an enhanced fungicidal activity. Further, the addition of PESA or its salt to a fungicidal azole compound provides enhancement of the fungicidal activity of the fungicidal azole compound as well as overcomes the negative effect of the fungicidal azole compound.

The invention claimed is:
1. A fungicidal composition comprising 5 to 100 grams of a fungicidal azole compound per 100 kilograms of seed and 0.5 to 99 times by weight the amount of the fungicidal azole compound of at least one compound selected from the group consisting of N-(2-phenylethyl)succinamic acid (PESA) and salts thereof.

2. The fungicidal composition according to claim 1, wherein the fungicidal azole compound is at least one azole selected from the group consisting of azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, penconazole, prochloraz, propiconazole, prothioconazole, simeconazole, tebuconazole, tetraconazole, triadimefon, triadimenol, triticonazole, and triflumizole.

3. The fungicidal composition according to claim 1, wherein the fungicidal azole compound is metconazole.

4. The fungicidal composition according to claim 3 that further comprises clothianidin and metalaxyl.

5. The fungicidal composition according to claim 1, wherein the amount of the fungicidal azole compound is 0.3 to 30% by weight, and the amount of PESA or its salts is 0.02 to 20% by weight of the fungicidal composition.

6. The fungicidal composition according to claim 1, comprising 0.3 to 30% by weight of the fungicidal azole compound, 0.02 to 20% by weight of N-(2-phenylethyl)succinamic acid or its salts, 50 to 99.5% of a carrier and 0.25 to 25% by weight of at least one auxiliary for formulation.

7. A method for enhancing fungicidal activity comprising applying the composition of claim 1 to a plant or soil.

8. The method according to claim 7, wherein the fungicidal azole compound is at least one azole selected from the group consisting of azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, penconazole, prochloraz, propiconazole, prothioconazole, simeconazole, tebuconazole, tetraconazole, triadimefon, triadimenol, triticonazole, and triflumizole.

9. The method according to claim 7, wherein the fungicidal azole compound is metconazole.

10. The method of according to claim 9 which further comprises applying clothianidin and metalaxyl.

11. The method according to claim 7, which comprises applying N-(phenylethyl)succinamic acid or its salts in combination with a fungicide azole compound to seed.

12. The method according to claim 11, wherein the fungicidal azole compound is at least one azole selected from the group consisting of azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, penconazole, prochloraz, propiconazole, prothioconazole, simeconazole, tebuconazole, tetraconazole, triadimefon, triadimenol, triticonazole, and triflumizole.

13. The method according to claim 11, wherein the fungicidal azole compound is metconazole.

14. A method for enhancing plant growth when an azole fungicide is used comprising applying the composition of claim 1 to a plant or soil.

15. The method according to claim 14, wherein the fungicidal azole compound is triadimenol.

* * * * *